United States Patent [19]

Suzukamo et al.

[11] Patent Number: 4,767,882

[45] Date of Patent: Aug. 30, 1988

[54] TETRAHYDRONAPHTHALENE DERIVATIVES AND THEIR PRODUCTION

[75] Inventors: Gohfu Suzukamo; Yoji Sakito, both of Osaka, Japan

[73] Assignee: Sumitomo Chemical Company, Limited, Osaka, Japan

[21] Appl. No.: 902,063

[22] Filed: Aug. 26, 1986

Related U.S. Application Data

[63] Continuation of Ser. No. 387,473, Jun. 11, 1982.

[30] Foreign Application Priority Data

| Jun. 11, 1981 | [JP] | Japan | 56-90657 |
| Jun. 15, 1981 | [JP] | Japan | 56-92671 |
| Jun. 16, 1981 | [JP] | Japan | 56-93313 |
| Jun. 18, 1981 | [JP] | Japan | 56-95075 |
| Jun. 23, 1981 | [JP] | Japan | 56-97843 |
| Jul. 8, 1981 | [JP] | Japan | 56-107331 |
| Aug. 12, 1981 | [JP] | Japan | 56-127224 |
| Aug. 12, 1981 | [JP] | Japan | 56-127225 |

[51] Int. Cl.⁴ .................................... C07C 69/76
[52] U.S. Cl. ...................... 560/100; 562/490; 568/715; 568/812; 570/183; 512/17; 512/19
[58] Field of Search ............. 560/100; 562/490; 568/715, 812; 570/183; 252/522 A

[56] References Cited

U.S. PATENT DOCUMENTS

| 3,499,751 | 3/1970 | Wood et al. | 71/123 |
| 3,927,083 | 12/1975 | Hall et al. | 252/522 R |
| 3,998,875 | 12/1976 | Tull | 562/466 |
| 4,097,674 | 6/1978 | Fried et al. | 562/490 |

*Primary Examiner*—Paul J. Killos
*Attorney, Agent, or Firm*—Birch, Stewart, Kolasch & Birch

[57] ABSTRACT

Tetrahydronaphthalene derivatives of the formula:

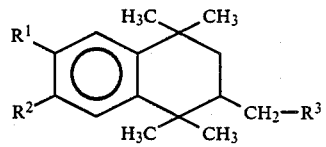

wherein either one of $R^1$ and $R^2$ is hydrogen, $C_1$-$C_4$ alkyl or $C_1$-$C_4$ alkoxy and the other is acetyl and $R^3$ is hydrogen or methyl in a racemic or optically active form, which are useful as perfumes or intermediates for production of perfumes, are prepared from an $R^4$-benzene and pyrocine through the intermediary compounds of the formula:

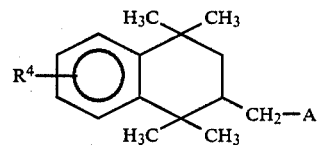

wherein $R^4$ is hydrogen, $C_1$-$C_4$ alkyl or $C_1$-$C_4$ alkoxy present at either one of 6- and 7-positions and A is hydrogen, carboxyl, $C_2$-$C_5$ alkoxycarbonyl, halogen, methyl, hydroxymethyl or halomethyl.

37 Claims, No Drawings

TETRAHYDRONAPHTHALENE DERIVATIVES AND THEIR PRODUCTION

This application is a continuation of application Ser. No. 387,473, filed on June 11, 1982.

The present invention relates to tetrahydronaphthalene derivatives and their production.

The objective tetrahydronaphthalene derivatives are representable by the formula:

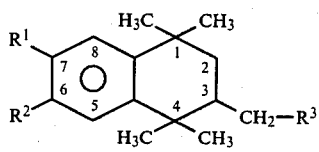
(I)

wherein either one of $R^1$ and $R^2$ is hydrogen, $C_1$-$C_4$ alkyl (e.g. methyl, ethyl, n-propyl, isopropyl, n-butyl, sec-butyl) or $C_1$-$C_4$ alkoxy (e.g. methoxy, ethoxy, n-propoxy, isopropoxy, n-butoxy, sec-butoxy) and the other is acetyl, and $R^3$ is hydrogen or methyl.

7-Acetyl-1,1,3,4,4,6-hexamethyl-1,2,3,4-tetrahydronaphthalene (I: $R^1$=COCH$_3$; $R^2$=CH$_3$; $R^3$=H) is a synthetic musky perfume known under the generic name "Tonalide" and can be produced by acetylation of 1,1,3,4,4,6-hexamethyl-1,2,3,4-tetrahydronaphthalene (hereinafter referred to as "HMT") (J. Org. Chem., 28, 2248 (1963)). For production of HMT, there are known reaction of p,α-dimethylstyrene with 2,3-dimethyl-2-butene or 3,3-dimethyl-2-butanol in the presence of an acid catalyst (U.S. Pat. Nos. 2,851,501 and 3,278,621) or with 2,3-dimethyl-1-butene in the presence of terra alba or a cation exchange resin (U.S. Pat. Nos. 3,379,784 and 3,379,785); reaction of 2-(p-tolyl)-2-halopropane with neohexene in the presence of aluminum chloride (U.S. Pat. No. 3,246,044); reaction of p-cymene with 2,3-dimethyl-2-butanol or 2,3-dimethyl-1-butene in the presence of an acid catalyst (J. Org. Chem., 28, 2248 (1963)) or with neohexene and a tertiary alkyl halide in the presence of aluminum chloride (U.S. Pat. No. 3,856,875 and Japanese Patent Publication (examined) No. 10057/1978), etc.

Since tonalide has an asymmetric carbon atom in its molecule, there are present two optical antipodes, i.e. (+)-isomer (R) and (−)-isomer (S). Tonalide obtained by any conventional procedure as above is a racemic mixture of those optical antipodes and has never been obtained in an optically active state.

In the field of medicines, agro-chemicals, insect hormones, food additives, etc., it is occasionally observed that one of the optical antipodes shows a significantly different property or activity from the other optical antipode. This is also true in the field of perfumes. For instance, the odor of Japanese mint oil is mainly originated in l-menthol. Further, for instance, the odor of caraway comes mainly from (+)-carvone. Furthermore, for instance, the major component for the odor of grape fruit is (+)-nootkatone. On the other hand, for instance, dextrorotatory carvone has the odor of caraway, and levorotatory carvone has the odor of Japanese mint oil. Thus, the odor of an optical antipode is hardly predictable from its racemic mixture with the other optical antipode. In other words, the successful production or separation of an optical antipode can provide a novel perfume, even when its racemic mixture with the other optical antipode and the odor of such racemic mixture are known.

As a result of an extensive study, the tetrahydronaphthalene derivatives (I) have now been successfully obtained in an optically active state by synthesizing them through some optically active precursors. When the precursors are in a racemic state, the produced tetrahydronaphthalene derivatives (I) are also in a racemic state. Thus, a novel process for production of the tetrahydronaphthalene derivatives, which include known and unknown substances, in a racemic or optically active state could be successfully established.

The said precursors in a racemic or optically active state are novel and can be represented by the formula:

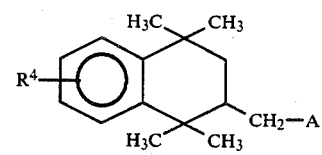
(II)

wherein $R^4$ is hydrogen, $C_1$-$C_4$ alkyl (e.g. methyl, ethyl, n-propyl, isopropyl, n-butyl, sec-butyl) or $C_1$-$C_4$ alkoxy (e.g. methoxy, ethoxy, n-propoxy, isopropoxy, n-butoxy, sec-butoxy) present at either one of the 6- and 7-positions and A is hydrogen, carboxyl, $C_2$-$C_5$ alkoxycarbonyl (e.g. methoxycarboxyl, ethoxycaronyl, n-propoxycarbonyl, isopropoxycarbonyl, n-butoxycaronyl, sec-butoxycarbonyl), halogen (e.g. chlorine, bromine, iodine), methyl, hydroxymethyl or halomethyl (e.g. chloromethyl, bromomethyl, iodomethyl).

The precursor tetrahydronaphthalene derivatives (II) include the following compounds:

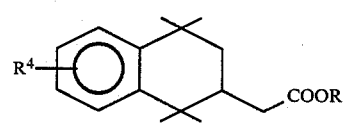
(IIa)

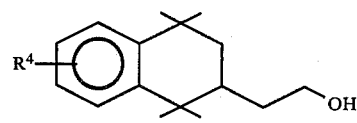
(IIb)

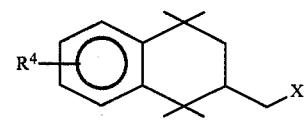
(IIc)

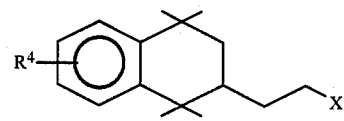
(IId)

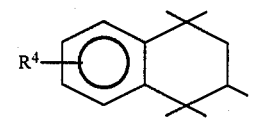
(IIe)

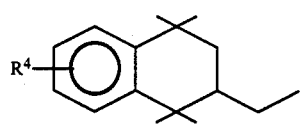

wherein $R^4$ is defined above, R is hydrogen or $C_1$-$C_4$ alkyl (e.g. methyl, ethyl, n-propyl, isopropyl, n-butyl, sec-butyl) and X is halogen (e.g. chlorine, bromine, iodine).

The objective and precursor tetrahydronaphthalene derivatives (I) and (II) can be produced from a benzene compound of the formula:

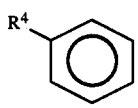

wherein $R^4$ is as defined above and 4-(2-methyl-1-propenyl)-5,5-dimethyltetrahydro-2-furanone (generic name "pyrocine") of the formula:

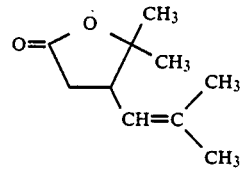

according to the following scheme:

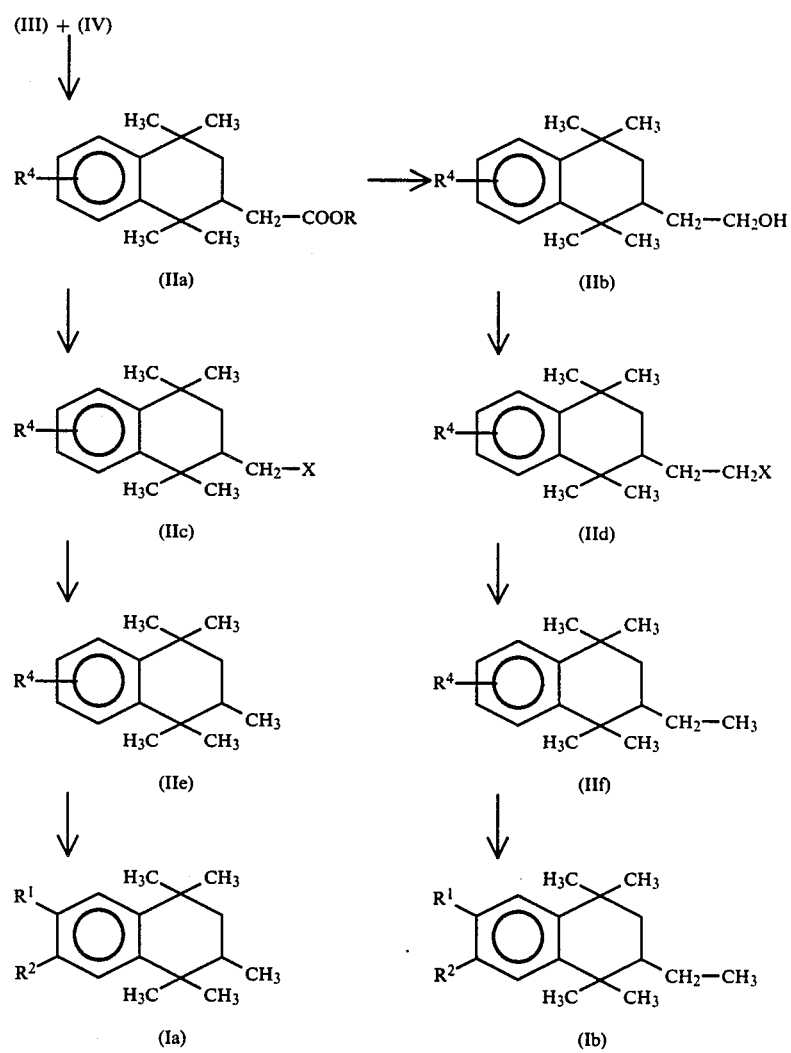

wherein R, $R^1$, $R^2$, $R^4$ and X are each as defined above.

Explaining the above conversions in detail, the initial step comprises the reaction between the benzene compound (III) and the pyrocine (IV) to give the acetic acid compound (IIa: R=H).

As the benzene compound (III), there may be used benzene, toluene, ethylbenzene, propylbenzene, butylbenzene, anisole, ethoxybenzene, propoxybenzene, butoxybenzene, etc. The pyrocine (IV) is known and can be prepared by ring opening of chrysanthemic acid under heating (Botyu Kagaku, 15, 1 (1950)) or by oxidizing 2,5-dimethyl-2,4-hexadiene to the corresponding monoepoxide and reacting the latter with a sodiomalonic ester, followed by hydrolysis (Tetrahedron Letters, 1845-1846 (1978)). The pyrocine (IV) in an optically active state is obtainable by heating optically active chrysanthemic acid (Agr. Biol. Chem., 34, 1115 (1970)).

The reaction may be effected by bringing the benzene compound (III) and the pyrocine (IV) into contact in the presence of a Friedel-Crafts catalyst. As the Friedel-Crafts catalyst, there may be used any Lewis acid conventionally employed in the Friedel-Crafts reaction. Specific examples are aluminum chloride, ferric chloride, etc. The Friedel-Crafts catalyst may be usually employed in an amount of an equimolar to three equivalent amounts with respect to the benzene compound (III). When the benzene compound is the one of the formula (III) wherein $R^4$ is hydrogen or $C_1$-$C_4$ alkyl, the amount of the Friedel-Crafts catalyst is normally from a equimolar to 1.5 equivalent amount, preferably from an equimolar to 1.2 equivalent amount, with respect to the pyrocine (IV). When the benzene compound is the one of the formula (III) wherein $R^4$ is $C_1$-$C_4$ alkoxy, the Friedel-Crafts catalyst may be used in a 2 to 3 equivalent amount, preferably in a 2 to 2.4 equivalent amount, with respect pyrocine (IV).

In effecting the reaction, there may be used any solvent for the reaction medium insofar as it does not afford any unfavorable influence on the proceeding of the reaction. When the benzene compound (III) wherein $R^4$ is hydrogen or $C_1$-$C_4$ alkyl is used in an excessive amount, it may serve as the reaction medium by itself. The reaction temperature is usually from $-20°$ C. to the boiling point of the benzene compound (III). A lower temperature is favorable for suppressing the production of any isomer, and an optimum range is usually between $-10°$ C. and $30°$ C. The reaction time is associated with the other reaction conditions and may be normally from 5 minutes to about 10 hours.

Alternatively, the reaction between the benzene compound (III) and the pyrocine (IV) may be conducted in the presence of an acid catalyst, followed by treatment of the resulting lactone compound of the formula:

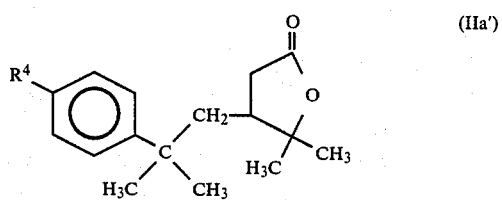

wherein $R^4$ is as defined above with a Friedel-Crafts catalyst to give the acetic acid compound (IIa: R=H).

As the acid catalyst, there may be exemplified sulfuric acid, phosphoric acid, p-toluenesulfonic acid, naphthalenesulfonic acid, etc. As the Friedel-Crafts catalyst, any conventional Lewis acid as exemplified hereinbefore may be employed.

In effecting the reaction at the initial stage, there may be used any inert solvent or an excessive amount of the benzene compound (III) for the reaction medium. The reaction temperature may be from $-30°$ C. to the boiling temperature of the benzene compound (III). The reaction time is usually within a range of 5 minutes to 10 hours.

The resulting lactone compound (IIa') may be then subjected to treatment with the Friedel-Crafts catalyst at the subsequent stage with or without its separation from the reaction mixture. The reaction conditions for such treatment are substantially the same as those in the said one step conversion of the benzene compound (III) and the pyrocine (IV) into the acetic acid compound (IIa: R=H).

In the above reaction between the benzene compound (III) and the pyrocine (IV), the optical activity in the pyrocine (IV) is maintained in the produced acetic acid compound (IIa: R=H) irrespective of whether the one step conversion or the two step conversion is adopted. For instance, the reaction of toluene (III: $R^4$=CH) with dextrorotatory pyrocine (IV) in ethanol gives the dextrorotatory acetic acid compound (IIa: R=H) (from benzene), while the reaction with levorotatory pyrocine (IV) in ethanol affords the levorotatory acetic acid compound (IIa: R=H) (from benzene).

In the above reaction, the reaction product usually comprises the acetic acid compound (IIa: R=H) having the substituent $R^4$ at the 6-position (i.e. the 6-position isomer) and the acetic acid compound (IIa: R=H) having the substituent $R^4$ at the 7-position (i.e. the 7-position isomer). Such position isomer mixture may be separated into each position isomer at this stage or subjected as such to any reaction in the subsequent step(s) and then separated into each position isomer at an appropriate stage. Separation can be accomplished in any per se conventional procedure such as recrystallization, chromatography or distillation. In this respect, it may be noted that the said two step conversion through the lactone compound (IIa') can yield predominantly the 6-position isomer and is therefore advantageous for the production of the objective and precursor tetrahydronaphthalene derivatives having the substituent $R^4$ at the 6-position.

Anyhow, it may be noted that the above procedure, irrespective of whether the one step conversion or the two step conversion is used, can afford the acetic acid compound (IIa: R=H) in a good yield and by one or two steps.

The conversion of the acetic acid compound (IIa: R=H) into the hydroxyethyl compound (IIb) is carried out by reduction of the former itself or of its alkyl ester (IIa: R=alkyl). The production of the alkyl ester (IIa: R=alkyl) can be readily accomplished by esterification of the acetic acid compound (IIa: R=H) in a per se conventional procedure.

The reduction of the acetic acid compound or its alkyl ester (IIa) to the hydroxyethyl compound (IIb) may be achieved by a reduction procedure conventionally adopted for conversion of a carboxyl or alkoxycarbonyl group into hydroxymethyl. A typical example of such procedure is the one using a metal hydride (e.g. aluminum hydride, lithium aluminum hydride, diborane), usually in an inert solvent (e.g. diethyl ether, tetrahydrofuran) at a temperature of $-10°$ C. to the boiling point of the inert solvent. When the metal hydride is aluminum hydride or diborane, such a low temperature as $-10°$ to $20°$ C. may be adopted for the reaction temperature.

The conversion of the acetic acid compound (IIa: R=H) into the halomethyl compound (IIc) is achieved by subjecting the former to halogenating decarboxylation.

The halogenating decarboxylation may be effected, for instance, by heating the acetic acid compound (IIa: R=H) in the presence of lead tetraacetate and an alkali metal halide, usually in an inert solvent. As the alkali metal halide, there may be employed sodium chloride, potassium chloride, lithium chloride, lithium bromide, lithium iodide, etc., among which lithium chloride is particularly preferred. Examples of the inert solvent are aromatic hydrocarbons (e.g. benzene, toluene), halogenated hydrocarbons (e.g. chloroform), acetonitrile, etc.

The amounts of lead tetraacetate and of the alkali metal halide (e.g. lithium chloride) may be respectively an equimolar amount or more with respect to the acetic acid compound (IIa: R=H). While the use of lead tetraacetate in an excessive amount is effective in enhancing the conversion, a larger amount over a 2 molar amount is rather unfavorable because of side reactions. For suppressing the progress of side reactions so as to achieve a higher selectivity, the use of lead tetraacetate in an equimolar amount or less is preferable. The use of lead tetraacetate as purified will afford a better result. A similar tendency to the above can be also observed with the alkali metal halide. Thus, its use in a larger amount than the equimolar amount is effective in increasing the conversion, while its use in a smaller amount than the equimolar amount is effective in increasing the selectivity. Normally, the alkali metal halide is employed in an amount of 0.5 to 3 mol to one mol of lead tetraacetate.

The reaction temperature may be normally from room temperature to 140° C., preferably from 30° to 100° C. The reaction time is varied with the other reaction conditions and may be usually from 30 minutes to 10 hours.

The conversion of the hydroxyethyl compound (IIb) into the haloethyl compound (IId) is attained by halogenation. Namely, the hydroxyethyl compound (IIb) may be reacted with a halogenating agent (e.g. thionyl chloride, phosphorus trichloride, phosphorus tribromide), usually in the presence of a tertiary amine (e.g. pyridine, triethylamine). When desired, any insert solvent may be used for the reaction medium. Examples of the inert solvent are aromatic hydrocarbons (e.g. benzene, toluene), halogenated hydrocarbons (e.g. chloroform, methylene chloride), etc. The reaction temperature depends upon the kind of the halogenating agent and may be usually not higher than the boiling temperature of the reaction system.

The conversion of the halomethyl compound (IIc) into the methyl compound (IIe) or of the haloethyl compound (IId) into the ethyl compound (IIf) may be accomplished by hydrogenolysis. Typical procedures for the hydrogenolysis are hydrogenation with a metal hydride, catalytic hydrogenation, etc.

In the hydrogenation with a metal hydride, the starting halogenated compound (IIc) or (IId) may be treated with a metal hydride (e.g. lithium hydride, lithium aluminum hydride) in an inert solvent (e.g. diethyl ether, tetrahydrofuran), usually at a temperature of 0° C. to the boiling temperature of the reaction system. The amount of the metal hydride may be usually from 0.1 to 2 mol to one mol of the starting compound. When, for instance, the metal hydride is lithium aluminum hydride, it may be used in an amount of ¼ to 2 mol, particularly of ½ to 1 mol, per one mol of the starting halogenated compound (IIc) or (IId). In case of the combined use of lithium hydride and of lithium aluminum hydride, it is favorable to use from 1 to 2 mol and from 0.1 to 0.5 mol, respectively thereof to one mol of the starting halogenated compound (IIc) or (IId).

In the catalytic hydrogenation, there may be used as a catalyst palladium, nickel, etc. A palladium catalyst is particularly preferred. The presence of a base in an equimolar amount with respect starting halogenated compound (IIc) or (IId) is favorable for carrying out the hydrogenation smoothly. Examples of the base are alkali metal salts of organic acids (e.g. sodium acetate, potassium acetate), tertiary amines (e.g. triethylamine, pyridine), amides (e.g. N,N-dimethylformamide, N,N-diethylformamide), etc. For the reaction medium, any inert solvent such as an alcohol (e.g. ethanol, isopropanol, t-butanol), an aromatic hydrocarbon (e.g. benzene, toluene) or an ether (e.g. tetrahydrofuran, dioxane) may be used.

The palladium catalyst may be in any conventional form such as a carrier type or a non-carrier type. Further, it may be employed in the form of a powder or in any shaped form. Examples of the catalyst of a non-carrier type are palladium black, palladium oxide, palladium chloride, etc. Examples of the catalyst of a carrier type are palladium-carbon, palladium-silica, palladium alumina, etc. The amount of the palladium catalyst is not limitative, and in the case of a batch system, it may be used in an amount of 0.001 to 1 equivalent, preferably of 0.01 to 0.2 equivalent, to one mol of the starting halogenated compound (IIc) or (IId).

Hydrogen to be used for the catalytic hydrogenation may be any conventional one which is available in the market. It may be used in an amount of not less than a stoichiometric amount. The hydrogenation can proceed under an atmospheric pressure, but an elevated pressure of not more than 150 atm is favorable. The temperature is usually not more than 100° C., preferably from about 10° to 80° C. A higher temperature is favorable for promotion of the reaction but may cause unfavorable side reactions.

The precursor compound (IIe) or (IIf) as obtained above can be then converted into the corresponding tetrahydronaphthalene derivative (Ia) or (Ib) by subjecting the former to acetylation.

The acetylation may be carried out by reacting the precursor compound (IIe) or (IIf) with an acetylating agent such as acetyl chloride, ketene or acetic anhydride in the presence of a Friedel-Crafts catalyst such as aluminum chloride or ferric chloride. The amount of the acetylating agent may be usually from 1.0 to 1.2 mol to one mol of the precursor compound (IIe) or (IIf). The amount of the Friedel-Crafts catalyst depends upon the kind of the acetylating agent and may be usually from 1.0 to 1.5 mol to one mol of acetyl chloride or ketene and from 2.0 to 2.5 mol to one mol of acetic anhydride. For the reaction medium, there may be used any inert solvent such as a halogenated hydrocarbon (e.g. dichloromethane, 1,2-dichloroethane), nitrobenzene or carbon disulfide. The reaction temperature may be not higher than the boiling point of the inert solvent as used, preferably from −10° to 30° C. The reaction time is varied with the reaction conditions and may be usually from 5 minutes to 10 hours In the above conversions, the progress of the reaction in each step may be monitored by application of any conventional analytical procedure such as gas chromatography, thin layer chromatography, IR absorption spectrum or NMR spectrum to a sample obtained from the reaction mixture.

Recovery of the product from the reaction mixture in each step may be accomplished by a per se conventional procedure such as distillation or extraction. Purification of the recovered product may be also accomplished by any per se known procedure such as distillation, recrystallization or chromatography.

When the pyrocine (IV) used as the starting material at the initial step has an optical activity, the products in the subsequent steps are optically active. When the pyrocine (IV) in a racemic state is employed, the product is a racemic mixture.

The racemic or optically active tetrahydronaphthalene derivatives (I) are generally useful as perfumes, particularly of high quality, good fixation and excellent stability. They are also useful as intermediates in the synthesis of perfumes, agro-chemicals, pharmaceuticals, etc. For instance, tonalide (I: $R^1$=COCH$_3$; $R^2$=CH$_3$; $R^3$=H) is known as a musky perfume. Further, for instance, 7-acetyl3-ethyl-,1,1,4,4,6-pentamethyl-1,2,3,4-tetrahydronaphthalene (I: $R^1$=COCH$_3$; $R^2$=CH ; $R^3$=CH$_3$), which is novel, is useful as a musky perfume.

It is noted that the use of the (R)-isomer of the acetic acid compound (IIa: R=H) affords (S)-tonalide, which has a strongly musky odor with a good fixation property, and the use of the (S)-isomer of the acetic acid compound (IIa: R=H) gives (R)-tonalide, which has a light and sweet aromatic odor. Advantageously, their use in combination with other aromatic chemicals in soaps, cosmetics, household compositions, perfumes, etc. does not produce any color change.

Practical and presently preferred embodiments of the invention are illustratively shown in the following Examples.

EXAMPLE 1

Production of optically active 3-carboxymethyl-1,1,4,4,6-pentamethyl-1,2,3,4-tetrahydronaphthalene (1) To a solution of (S)-4-(2-methyl-1-propenyl)-5,5-dimethyltetrahydro-2-furanone ($[\alpha]_D$ -62.5° (C=0.5 in ethanol)) (2.50 g; 14.9 mmol) in toluene (30 ml), anhydrous aluminum chloride (2.10 g; 15.8 mmol) was added, and the resultant mixture was stirred at 10° C. for 5 hours. The reaction mixture was admixed with 18% hydrochloric acid (10 ml) and separated. The organic layer was washed with dilute hydrochloric acid and extracted with 5% ammonia water. The extract was treated with 50% sulfuric acid and shaken with toluene. The toluene layer was washed with saturated sodium chloride solution, dried over anhydrous sodium sulfate and concentrated under reduced pressure. The product ($[\alpha]_{546}$ −23.8° (C=1 in benzene)) (3.79 g) was dissolved in n-hexane under heating and then cooled. The precipitated crystals were separated by filtration, and the filtrate was concentrated to give (R)-3-carboxymethyl-1,1,4,4,6-pentamethyl-1,2,3,4-tetrahydronaphthalene (3.42 g; 13.2 mmol; 88%). $[\alpha]_{546}$ −26.2° (C=1 in benzene).

NMR (CDCl$_3$) δ (ppm): 1.10 (3H, s), 1.28 (6H, s), 1.34 (3H, s), 2.30 (3H, s), 1.54–2.83 (5H, m), 6.86–7.31 (3H, m), 12.17 (1H, s).

IR (cm$^{-1}$): 1705 (C=0).

(2) In the same manner as in Example 1 (1) but using (R)-4-(2-methylpropenyl)-5,5-dimethyltetrahydro-2-furanone ($[\alpha]_D$ +62.5° (C=0.5 in ethanol)) (2.50 g; 14.9.mmol), there was obtained (S)-3-(carboxymethyl)-1,1,4,4,6-pentamethyl-1,2,3,4-tetrahydronaphthalene (3.35 g; 12.9 mmol; 86%). $[\alpha]_{546}$ +26.3° (C=1 in benzene).

The NMR and IR spectra of the product were identical to those of the product in Example 1 (1).

(3) To a solution of (R)-4-(2-methylpropenyl)5,5-dimethyltetrahydro-2-furanone ($[\alpha]_D$ +62.0° (C=0.54 in ethanol)) (0.35 g; 2.08 mmol) in toluene (10 ml), conc. sulfuric acid (0.3 ml) was added, and the resultant mixture was stirred at room temperature for 1 hour. The toluene layer was washed with sodium hydroxide solution, dried over anhydrous sodium sulfate and concentrated under reduced pressure to give (S)-5,5-dimethyl-4-(2-methyl-2-p-tolylpropyl)-tetrahydro-2-furanone (0.27 g; 50%). $[\alpha]_{546}$ +50.5° (C=1.03 in benzene).

NMR (CDCl$_3$) δ (ppm): 1.16 (3H, s), 1.29 (3H, s), 1.30 (6H, s), 1.60–1.85 (5H, m), 2.28 (3H, s), 7.04 (4H, s).

IR (cm$^{31\ 1}$): 1760.

(4) To a solution of (S)-5,5-dimethyl-4-(2-methyl-2-p-tolylpropyl)-tetrahydro-2-furanone (100 mg) in toluene (10 ml), anhydrous aluminum chloride (130 mg) was added, and the resultant mixture was stirred at 70° C. for 30 minutes. The reaction mixture was washed with dilute hydrochloric acid, dried and concentrated to give (S)-3-carboxymethyl-1,1,4,4,6-pentamethyl-1,2,3,4-tetrahydronaphthalene (95 mg).

The NMR spectrum of the product was identical to that of the product in Example 1 (1). $[\alpha]_{546}$ +26.3° (C=1 in benzene).

EXAMPLE 2

Production of 2-carboxymethyl-1,1,4,4,6-pentamethyl-1,2,3,4-tetrahydronaphthalene To a solution of 4-(2-methylpropenyl)-5,5-dimethyltetrahydro-2-furanone (16.6 g; 98.8 mmol) in toluene (200 ml), anhydrous aluminum chloride (15.8 g; 118.5 mmol) was added, and the resultant mixture was stirred at 70° C. for 2 hours. The reaction mixture was admixed with 18% hydrochloric acid (70 ml). The organic layer was separately washed with dilute hydrochloric acid and extracted with 5% ammonia. The extract was treated with dilute sulfuric acid and shaken with toluene. The toluene layer was washed with saturated sodium chloride solution, dried over anhydous sodium sulfate and concentrated under reduced pressure. The product (25.17 g) was recrystallized from n-hexane to give 2-carboxymethyl-1,1,4,4,6-pentamethyl-1,2,3,4-tetrahydronaphthalene (4.37 g; 16.8 mmol; 17%).

NMR (CDCl$_3$) δ (ppm): 1.08 (3H, s), 1.31 (6H, s), 1.35 (3H, s), 2.30 (3H, s), 1.53–2.83 (5H, m), 6.87–7.30 (3H, m), 12.17 (1H, s).

IR (cm$^{-1}$): 1705.

The mother liquor on recrystallization was concentrated to give a mixture of position isomers (20.8 g).

EXAMPLE 3

Production of 3-carboxymethyl-6 or 7-methoxy-1,1,4,4-tetramethyl-1,2,3,4-tetrahydronaphthalene To anhydrous aluminum chloride (7.50 g; 54.9 mmol) a solution of pyrocine (4.19 g; 24.95 mmol) and anisole (2.70 g; 24.95 mmol) in ethylene dichloride (30 ml) was added dropwise, and the resultant mixture was heated gradually to 70° C. and then stirred at 70° C. for 30 minutes. After cooling, dilute hydrochloric acid was added thereto. The organic layer was separated and extracted with sodium hydroxide solution. The extract was acidified with hydrochloric acid and extracted with ethyl acetate. The extract was washed with saturated sodium chloride solution, dried over anhydrous sodium sulfate and concentrated under reduced pressure. Purification of the product with silica gel chromatography gave 6-or 7-methoxy-1,1,4,4-tetramethyl-1,2,3,4-tetrahydronaphthalene-2-acetic acid (4.31 g; 15.6 mmol. 62.6%).

NMR (CDCl$_3$) δ (ppm): 1.08, 1.10 (3H, s), 1.26, 1.29, 1.31, 1.34, 1.35 (9H, s), 1.57–1.72 (2H, m), 2.06–2.40 (2H, m), 2.66–2.74 (1H, m), 6.70–7.28 (3H, m).

EXAMPLE 4

Production of optically active 1,1,3,4,4,6-hexamethyl-1,2,3,4-tetrahydronaphthalene (1) To a solution of (R)-3-carboxymethyl1,1,4,4,6-pentamethyl-1,2,3,4-tetrahydronaphthalene ($[\alpha]_{546}$ $-23.8°$ (C=1 in benzene)) (2.00 g; 7.69 mmol) in benzene (30 ml), lead tetraacetate (4.00 g; 9.02 mmol) and anhydrous lithium chloride (0.80 g; 18.9 mmol) were added, and the resultant mixture was refluxed for 6 hours. The reaction mixture was washed with water, dilute hydrochloric acid and 6% ammonia water in order. The benzene layer was dried, concentrated and purified on column chromatography to give (S)-3-chloromethyl-1,1,4,4,6-pentamethyl-1,2,3,4-tetrahydronaphthalene (1.22 g; 4.87 mmol). From the ammonia water layer, there was recovered the unreacted carboxylic acid (0.35 g; 1.34 mmol). The yield was 77% (based on the consumed carboxylic acid). $[\alpha]_{546}$ $+26.1°$ (C=1 in n-hexane).

NMR (CCl$_4$) δ (ppm): 1.08 (3H, s), 1.24 (3H, s), 1.50 (3H, s), 1.39 (3H, s), 1.48–1.95 (3H, m), 3.23 (1H, t), 3.87 (1H, dd), 6.77–7.20 (3H, m).

(2) In the same manner as in Example 1 (1) but using (S)-3-(carboxymethyl)-1,1,4,4,6-pentamethyl-1,2,3,4-tetrahydronaphthalene ($[\alpha]_{546}$ $-23.8°$ (C=1 in benzene)), there was prepared (R)-3-chloromethyl-1,1,4,4,6-pentamethyl-1,2,3,4-tetrahydronaphthalene ($[\alpha]_{546}$ $-26.2°$ (C=1 in n-hexane). The NMR spectrum of the product was identical to that of the product in Example 4 (1).

(3) To a suspension of lithium aluminum hydride (9.56 g; 0.252 mol) in tetrahydrofuran (70 ml) under a nitrogen stream, a solution of (S)-3-chloromethyl-1,1,4,4,6-pentamethyl-1,2,3,4-tetrahydronaphthalene ($[\alpha]_{546}$ 26.1° (C=1 in n-hexane)) (62.9 g; 0.251 mol) in tetrahydrofuran was dropwise added. After refluxing for 15 hours, the reaction mixture was treated with aqueous tetrahydrofuran in nitrogen, admixed with 5% hydrochloric acid (600 ml) and extracted with n-hexane. The extract was washed with saturated sodium chloride solution, dried, concentrated and distilled to give (S)-1,1,3,4,4,6-hexamethyl-1,2,3,4-tetrahydronaphthalene (46.0 g; 0.213 mol; 85%). $[\alpha]_{546}$ $-49.1°$ (C=1 in chloroform). B.P., 91° C./0.5 mmHg.

NMR (CCl$_4$) δ (ppm): 0.96 (3H, d), 1.03 (3H, s), 1.21 (3H, s), 1.24 (3H, s), 1.28 (3H, s), 1.34–1.86 (3H, m), 2.25 (3H, s), 6.71–7.14 (3H, m).

(4) In the same manner a in Example 4 (3) but using (R)-3-chloromethyl-1,1,4,4,6-pentamethyl-1,2,3,4-tetrahydronaphthalene ($[\alpha]_{546}$ $-26.2°$ (C=1 in n-hexane)), there was obtained (R)-1,1,3,4,4,6-hexamethyl-1,2,3,4-tetrahydronaphthalene ($[\alpha]_{546}$ $+48.9°$ (C=1 in chloroform)). B.P., 91° C./0.5 mmHg. The NMR spectrum of this product was identical to that of the product in Example 4 (3).

(5) Into an autoclave, (S)-3-(chloromethyl)-1,1,4,4,6-pentamethyl-1,2,3,4-tetrahydronaphthalene 200 mg; 0.798 mmol), isopropanol (10 ml), sodium acetate trihydrate (120 mg; 0.882 mmol) and 10 % palladium carbon (160 mg) were charged, and the resultant mixture was stirred at 50° C. under a hydrogen pressure of 80 kg/cm$^2$ for 12 hours. After cooling, the reaction mixture was filtered to separate palladium carbon, admixed with water and extracted with n-hexane. The extract was washed with saturated sodium hydrogen carbonate solution, dried and concentrated to give (S)-1,1,3,4,4,6-hexamethyl-1,2,3,4-tetrahydronaphthalene (172 mg; 0.796 mmol).

(6) To a suspension of lithium hydride (4.52 g; 0.569 mol) and aluminum lithium hydride (1.81 g; 0.048 mol) in tetrahydrofuran under nitrogen, (S)-3-chloromethyl-1,1,4,4,6-pentamethyl-1,2,3,4-tetrahydronaphthalene (94.69 g; 0.378 mol) was added dropwise, and the resultant mixture was heated while refluxing for 36 hours. The reaction mixture was treated with dilute hydrochloric acid and extracted with n-hexane. The extract was washed with saturated sodium chloride solution, dried, concentrated and distilled to give (S)-1,1,3,4,4,6-hexamethyl-1,2,3,4-tetrahydronaphthalene (59.7 g; 0.276 mol).

EXAMPLE 5

Production of 1,1,2,4,4,6-hexamethyl-1,2,3,4-tetrahydronaphthalene (1) To a solution of 2-carboxymethyl-1,1,4,4,6-pentamethyl-1,2,3,4-tetrahydronaphthalene (30 g; 0.115 mol) in benzene (570 g), lead tetraacetate (66 g; 0.149 mol) and anhydrous lithium chloride (11.5 g; 0.271 mol) were added, and the temperature was elevated up to 80° C. After stirring for 6.5 hours, the reaction mixture was washed with water and dilute hydrochloric acid in order. After extraction of the unreacted carboxylic acid with 6% ammonia water, the benzene layer was dried over anhydrous sodium sulfate and concentrated to give 2-chloromethyl-1,1,4,4,6-pentamethyl-1,2,3,4-tetrahydronaphthalene (18.9 g; 0.075 mol). From the ammonia water layer, there was recovered the unreacted carboxylic acid (9.8 g).

NMR(CCl$_4$) δ (ppm): 1.08 (3H, s), 1.24 (3H, s), 1.32 (3H, s), 1.39 (3H, s), 1.48–1.95 (3H, m), 3.23 (1H, t), 3.87 (1H, dd), 6.77–7.20 (3H, m).

(2) To a suspension of lithium aluminum hydride (6.5 g; 0.171 mol) in tetrahydrofuran in a nitrogen atmosphere, a solution of 2-chloromethyl-1,1,4,4,6-pentamethyl1,2,3,4-tetrahydronaphthalene (40.9 g; 0.163 mol) in tetrahydrofuran was added dropwise, and the resultant mixture was stirred at 70° C. for 15 hours. The reaction mixture was treated with aqueous tetrahydrofuran, dilute hydrochloric acid was added thereto, and the resultant mixture was extracted with n-hexane. The extract was washed with saturated sodium chloride solution, dried over anhydrous sodium sulfate and concentrated to give 1,1,2,4,4,6-hexamethyl-1,2,3,4-tetrahydronaphthalene (31.6 g; 0.144 mol; 88%). B.P., 78° C./1.2 mmHg. M.P., 35°–36° C.

NMR (CCl$_4$) δ (ppm): 0.95 (3H, d), 1.01 (3H, s), 1.21 (3H, s), 1.25 (6H, s), ~1.85 (3H, m), 2.23 (3H, s), 6.63–7.12 (3H, m).

EXAMPLE 6

Production of optically active 3-ethyl-1,1,4,4,6-pentamethyl-1,2,3,4-tetrahydronaphthlene (1) A suspension of lithium aluminum hydride (16.8 g; 0.442 mol) in tetrahydrofuran (200 ml) was heated up to 60° C., a solution of (S)-3-carboxymethyl-1,1,4,4,6-pentamethyl-1,2,3,4-tetrahydronapthalene ($[\alpha]_{546}$ $+25.3°$ (C=1 in benzene)) (76.4 g; 0.294 mol) in tetrahydrofuran was added dropwise thereto. The resultant mixture was stirred at 60° C. for 2 hours. The reaction mixture was cooled, treated with dilute hydrochloric acid and extracted with toluene (200 ml). The extract was washed with dilute hydrochloric acid, saturated sodium carbonate solution and saturated sodium chloride solution in order, dried over anhydrous sodium sulfate and concentrated to give (S)-3-(2-hydroxyethyl)-1,1,4,4,6-pentamethyl-1,2,3,4-tetrahydronaphthalene (70.5 g; 0.28 mol; 97.5%). $[\alpha]_{546} -8.1°$ (C=0.62 in ethanol).

NMR (CCl$_4$) δ (ppm): 1.04 (3H, s), 1.20 (3H, s), 1.25 (3H, s), 1.30 (3H, s), 1.44–1.97 (5H, m), 2.25 (3H, s), 3.17 (1H, s), 3.44–3.75 (2H, m), 6.73–7.30 (3H, m).

(2) In the same manner as in Example 4 (1) but using (R)-3-carboxymethyl-1,1,4,4,6-pentamethyl-1,2,3,4-tetrahydronaphthalene ($[\alpha]_{546} -24.1°$ (C=1 in benzene)), there was prepared (R)-3-(2-hydroxyethyl)-1,1,4,4,6-pentamethyl-1,2,3,4-tetrahydronaphthalene. $[\alpha]_{546} +8.3°$ (C=0.965 in ethanol). The NMR spectrum of the product was identical to that of the product in Example 6 (1).

(3) (S)-3-(2-Hydroxyethyl)-1,1,4,4,6-pentamethyl-1,2,3,4-tetrahydronaphthalene ($[\alpha]_{546} -8.1°$ (C=0.62 in ethanol)) (70.5 g; 0.287 mol) was dissolved in toluene (700 g), and pyridine (25.0 g; 0.316 mol) was added thereto. The resulting mixture was cooled to 0° C., and thionyl chloride (41.0 g; 0.345 mol) was added dropwise thereto. After the addition was completed, the resultant mixture was heated at 60° C. for 5 hours. The reaction mixture was cooled, washed with dilute hydrochloric acid, saturated sodium carbonate solution and saturated sodium chloride solution in order, dried over anhydrous sodium sulfate and concentrated to give (S)-3-(2-chloroethyl)-1,1,4,4,6-pentamethyl-1,2,3,4-tetrahydronaphthalene (46.5 g; 0.176 mol; 61%). B.P., 106°–107° C./0.13 mmHg. $[\alpha]_{546} -33.4°$ (C=1.2 in ethanol).

NMR (CCl$_4$) δ (ppm): 1.06(3H, s), 1.23 (3H, s), 1.27 (3H, s), 1.32 (3H, s), 1.45–1.98 (5H, m), 2.28 (3H, s), 3.49–3.75 (2H, m), 6.79–7.23 (3H, m).

(4) In the same manner a in Example 6 (3) but using a solution of (R)-3-(2-hydroxyethyl)-1,1,4,4,6-pentamethyl-1,2,3,4-tetrahydronaphthalene, there was obtained (R)-3-(2-chloroethyl)-1,1,4,4,6-pentamethyl-1,2,3,4-tetrahydronaphthalene ($[\alpha]_{546} +33.1°$ (C=1.1 in ethanol)).

The boiling point and the NMR spectrum of the product were identical to those of the product in Example 6 (3).

(5) To a suspension of aluminum lithium hydride (6.5 g; 0.171 mol) in tetrahydrofuran (100 ml), a solution of (S)-3-(2-chloroethyl)-1,1,4,4,6-pentamethyl-1,2,3,4-tetrahydronaphthalene ($[\alpha]_{546} -33.4°$ (C=1.17 in ethanol)) (44.8 g; 0.169 mol) in tetrahydrofuran was dropwise added thereto. The resultant mixture was heated with reflux for 12 hours and then cooled. The cooled mixture was treated with dilute hydrochloric acid and extracted with n-hexane. The extract was washed with saturated sodium chloride solution, dried over anhydrous sodium sulfate and concentrated to give (R)-3-ethyl-1,1,4,4,6-pentamethyl-1,2,3,4-tetrahydronaphthalene (37.0 g; 0.161 mol; 94%). B.P., 79°–80° C./0.15 mmHg. $[\alpha]_{546} +2.2°$ (C=0.95 in ethanol).

NMR (CCl$_4$) δ (ppm): 1.00 (3H, t), 1.02 (3H, s), 1.19 (3H, s), 1.27 (6H, s), 1.43–1.80 (5H, m), 2.23 (3H, s), 6.60–7.08 (3H, m).

(6) In the same manner as in Example 4 (5) but using (R)-3-(2-chloroethyl)-1,1,4,4,6-pentamethyl-1,2,3,4-tetrahydronaphthalene, there was obtained (S)-3-ethyl-1,1,4,4,6-pentamethyl-1,2,3,4-tetrahydronaphthalene. The boiling point and the NMR spectrum of the product were identical to those of the product in Example 6 (5). $[\alpha]_{546} -2.0°$ (C=1.1 in ethanol).

EXAMPLE 7

Production of optically active 7-acetyl-1,1,3,4,4,6-hexamethyl-1,2,3,4-tetrahydronaphthalene (1) To a solution of (S)-1,1,3,4,4,6-hexamethyl1,2,3,4-tetrahydronaphthalene ($[\alpha]_{546} -49.1°$ (C=1 in n-hexane)) (100.0 g; 0.463 mol) in 1,2-dichloroethane (300 g), acetyl chloride (38.0 g; 0.484 mol) and anhydrous aluminum chloride (71.0 g; 0.533 mol) were added, and the resultant mixture was stirred at 20° C. for 1 hour. The reaction mixture was treated with 10% hydrochloric acid (300 ml) and then separated into a water layer and an organic layer. The organic layer was washed with dilute hydrochloric acid and saturated sodium carbonate solution, dried and concentrated to give (S)-7-acetyl-1,1,3,4,4,6-hexamethyl-1,2,3,4-tetrahydronaphthalene (107.5 g; 0.417 mol; 90%). B.P., 109° C./0.2 mmHg. $[\alpha]_{546} -36.9°$ (C=1 in ethanol).

NMR (CCl$_4$) δ (ppm): 0.98 (3H, d), 1.06 (3H, s), 1.26 (3H, s), 1.30 (6H, s), 1.40–1.87 (3H, m), 2.45 (3H, s), 2.49 (3H, s), 7.06 (1H, s), 7.54 (1H, s).

(2) In the same manner as in Example 7 (1) but using (R)-1,1,3,4,4,6-hexamethyl-1,2,3,4-tetrahydronaphthalene ($[\alpha]_{546} +48.9°$ (C=1 in chloroform)), there was obtained (R)-7-acetyl-1,1,3,4,4,7-hexamethyl-1,2,3,4-tetrahydronaphthalene. B.P., 109° C./0.2 mmHg. $[\alpha]_{546} +36.2°$ (C=1 in ethanol).

EXAMPLE 8

Production of 7-acetyl-1,1,2,4,4,6-hexamethyl-1,2,3,4-tetrahydronaphthalene

To a solution 1,1,2,4,4,6-hexamethyl-1,2,3,4-tetrahydronaphthalene (21.0 g; 0.097 mol) and acetyl chloride (8.0 g; 0.102 mol) in dichloroethane (60 g), anhydrous aluminum chloride (14.9 g; 0.112 mol) was added, and the resulting mixture was stirred at room temperature for 1 hour. The reaction mixture was treated with dilute hydrochloric acid. The organic layer was separated, washed with dilute hydrochloric acid, saturated sodium carbonate solution and saturated sodium chloride solution, dried and concentrated to give 7-acetyl-1,1,2,4,4,6-hexamethyl-1,2,3,4-tetrahydronaphthalene (19.3 g; 0.075 mol; 77%). B.P., 109° C./0.2 mmHg. M.P., 61.5°–62.5° C.

NMR (CCl$_4$) δ (ppm): 0.98 (3H, d), 1.05 (3H, s), 1.23 (3H, s), 1.27 (3H, s), 1.33 (3H, s), 1.40–1.93 (3H, m), 2.42 (3H, s), 2.47 (3H, s), 6.98 (1H, s), 7.58 (1H, s).

EXAMPLE 9

Production of optically active 7-acetyl-3-ethyl-1,1,4,4,6-pentamethyl-1,2,3,4-tetrahydronaphthalene (1) To a solution of (R)-3-ethyl-1,1,4,4,6-pentamethyl-1,2,3,4-tetrahydronaphthalene ($[\alpha]_{546} +2.2°$ (C=0.95 in ethanol)) (36.5 g; 0.159 mol) and acetyl chloride (13.7 g; 0.174 mol) in 1,2-dichloroethane (100 ml), anhydrous aluminum chloride (25.3 g; 0.190 mol) was added at 20° C., and the resulting mixture was stirred for 1 hour. The reaction mixture was treated with dilute hydrochloric acid while cooling with ice. The organic layer was washed with dilute hydrochloric acid, saturated sodium carbonate solution and saturated sodium chloride solution in order, dried over anhydrous sodium sulfate and concentrated t give (R)-7-acetyl-3-ethyl-1,1,4,4,6-pentamethyl-1,2,3,4-tetrahydronaphthalene (41.5 g; 0.153 mol; 96%). B.P., 120° C./0.1 mmHg. [α]₃₆₅ −46.1° (C=0.97 in ethanol).

NMR (CCl₄) δ (ppm): 1.01 (3H, t), 1.04 (3H, s), 1.23 (3H, s), 1.31 (6H, s), 1.46-1.93 (5H, m), 2.41 (3H, s), 2.44 (3H, s), 7.03 (1H, s), 7.53 (1H, s).

(2) In the same manner as in Example 9 (1) but using (S)-3-ethyl-1,1,4,4,6-pentamethyl-1,2,3,4-tetrahydronaphthalene ([α]₅₄₆ −2.0° (C=1.1 in ethanol)), there was obtained (S)-7-acetyl-3-ethyl-1,1,4,4,6-pentamethyl-1,2,3,4-tetrahydronaphthalene. The boiling point and the NMR spectrum of the product were identical to those of the product in Example 9 (1). [α]₃₆₅ +45.4° (C=1 in ethanol).

What is claimed is:

1. A process for preparing a compound of the formula:

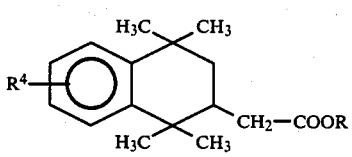

wherein R is hydrogen or $C_1$-$C_4$ alkyl and $R^4$ is hydrogen, $C_1$-$C_4$ alkyl or $C_1$-$C_4$ alkoxy present at either one of the 6-or 7-positions, which comprises (a) reacting a benzene compound of the formula:

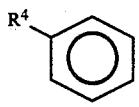

wherein $R^4$ is as defined above with pyrocine of the formula:

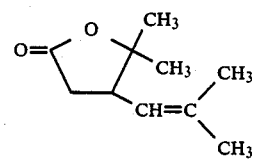

in the presence of a Friedel-Crafts catalyst or (b) reacting said benzene compound with said pyrocine in the presence of an acid catalyst and treating the resultant product with a Friedel-Crafts catalyst.

2. process for preparing a compound of the formula:

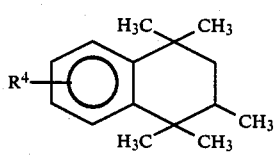

wherein $R^4$ is hydrogen, $C_1$-$C_4$ alkyl or $C_1$-$C_4$ alkoxy present at either one of the 6- and 7-positions, which comprises subjecting the product according to claim 1 to halogenating decarboxylation and subjecting the resultant product to hydrogenolysis.

3. A process for preparing a compound of the formula:

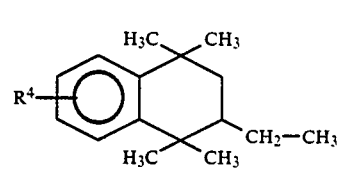

wherein $R^4$ is hydrogen, $C_1$-$C_4$ alkyl, or $C_1$-$C_4$ alkoxy present at either one of the 6- and 7-positions, which comprises subjecting the product according to claim 1 to reduction, subjecting the resultant product to halogenation and subjecting the resulting product to hydrogenolysis.

4. A process for preparing a compound of the formula:

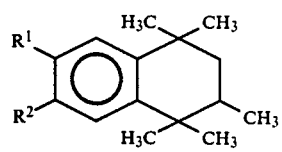

wherein either one of $R^1$ and $R^2$ is hydrogen, $C_1$-$C_4$ alkyl or $C_1$-$C_4$ alkoxy and the other is acetyl, which comprises subjecting the product according to claim 2 to acetylation.

5. A process for preparing a compound of the formula:

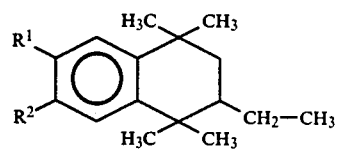

wherein either one of $R^1$ and $R^2$ is hydrogen, $C_1$-$C_4$ alkyl or $C_1$-$C_4$ alkoxy and the other is acetyl, which comprises subjecting the product according to claim 3 to acetylation.

6. A compound of the formula:

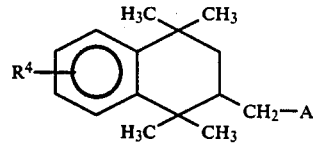

wherein $R^4$ is hydrogen, $C_1$-$C_4$ alkyl or $C_1$-$C_4$ alkoxy present at either one of the 6- and 7-positions and A is hydrogen, carboxyl, $C_2$-$C_5$ alkoxycarbonyl, halogen, methyl, hydroxymethyl or halomethyl, provided that when $R^4$ is hydrogen or $C_1$-$C_4$ alkyl, A is not hydrogen or methyl.

7. The compound according to claim 6, wherein A is $C_2$-$C_5$ alkyoxycarbonyl.

8. The compound according to claim 6, wherein A is hydroxymethyl.

9. The compound according to claim 6, wherein A is halogen.

10. The compound according to claim 6, wherein A is halomethyl.

11. The compound according to claim 6, wherein A is hydrogen.

12. A compound of the formula:

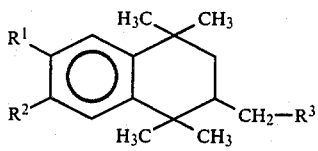

wherein either one of $R^1$ and $R^2$ is $C_1$-$C_4$ alkoxy and the other is acetyl and $R^3$ is hydrogen or methyl in an optically active or racemic form.

13. A process for preparing a compound of the formula:

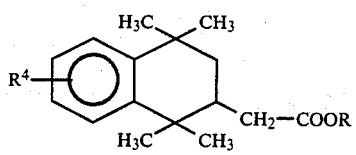

wherein R is hydrogen or $C_1$-$C_4$ alkyl and $R^4$ is hydrogen, $C_1$-$C_4$ alkyl or $C_1$-$C_4$ alkoxy present at either one of the 6- or 7-positions, which comprises, in a single step, reacting a benzene compound of the formula:

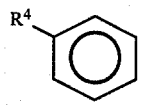

wherein $R^4$ is as defined above with pyrocine of the formula:

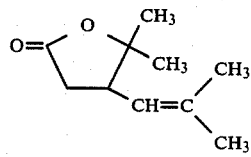

in the presence of a Friedel-Crafts catalyst.

14. The process of claim 1 or claim 13, further comprising the step of esterifying the resulting product.

15. The process of claim 1 or claim 13, wherein the Friedel-Crafts catalyst is a Lewis acid.

16. The process of claim 15, wherein said Lewis acid is aluminum chloride or ferric chloride.

17. The process of claim 13, wherein the Friedel-Crafts catalyst is employed in an amount ranging from equimolar to three equivalents with respect to the amount of said benzene compound.

18. The process of claim 17, wherein the reaction is carried out at a temperature between $-10°$ C. and $30°$ C.

19. The process of claim 1, wherein the acid catalyst is sulfuric acid, phosphoric acid, p-toluendsulfonic acid or naphthalenesulfonic acid.

20. The process of claim 1, wherein the reaction in the presence of a Friedel-Crafts catalyst is carried out at a temperature of $-10°$ C. to $30°$ C.

21. The process of claim 1, wherein the reaction in the presence of an acid catalyst is carried at a temperature of from $-10°$ C. to $150°$ C. and said reaction in the presence of a Friedel-Crafts catalyst is carried out at a temperature of from $-10°$ C. to $30°$ C.

22. The process of claim 2, wherein said halogenating decarboxylation is carried out by treatment with lead tetraacetate and an alkali metal halide in an inert solvent at a temperature of $30°$ C. to $100°$ C.; and said hydrogenolysis is carried out by treatment with a metal hydride in an inert solvent at a temperature of $0°$ C. to the boiling temperature of the reaction system or is carried out by treatment with hydrogen in the presence of a palladium catalyst in an inert solvent at a temperature of $10°$ C. to $80°$ C.

23. The process of claim 22, wherein said alkali metal halide in said halogenating decarboxylation step is sodium chloride, postassium chloride, lithium chloride, lithium bromide or lithium iodide.

24. The process of claim 22, wherein said metal hydride is said hydrogenolysis step is lithium hydride or lithium aluminum hydride.

25. The process of claim 22, wherein said palladium catalyst in said hydrogenolysis step is a member selected from the group consisting of palladium black, palladium oxide, palladium chloride, palladium-carbon, palladium-silica and palladium alumina.

26. The process of claim 2, wherein said reduction is carried out by treatment with a metal hydride in an inert solvent at a tempeature of $-10°$ C. to the boiling point of the inert solvent; said halogenation is carried out by treatment with a halogenating agent in an inert solvent in the presence of a teritary amine at a temperature of not higher than the boiling temperature of the reaction system; and said hydrogen olysis is carried out by treatment with a metal hydride in an inert solvent at $0°$ C. to the boiling temperature of the reaction system or is carried out by treatment with hydrogen in the presence of a palladium catalyst in an inert solvent at a temperature of $10°$ C. to $80°$ C.

27. The process of claim 26, wherein said metal hydride in said reduction step is aluminum hydride, lithium aluminum hydride or diborane.

28. The process of claim 26, wherein said halogenating agent in said halogenation step is thionyl chloride, phosphorus trichloride or phosphorus tribromide.

29. The process of claim 26, wherein said metal hydride in said hydrogenolysis step is lithium hydride or lithium aluminum hydride.

30. The process of claim 26, wherein said palladium catalyst in the hydrogenolysis is palladium black, palladium oxide, palladium chloride, palladium-carbon, palladium-silica or palladium alumina.

31. The process of claim 4, wherein said acetylation is carried out by reacting with acetyl chloride, ketone or acetic anhydride in the presence of a Friedel-Crafts catalyst in an inert solvent at a temperature of $-10°$ C. to $30°$ C.

32. The process of claim 31, wherein the Friedel-Crafts catalyst is aluminum chloride or ferric chloride.

33. The process of claim 5, wherein said acetylation is carried out by reacting with acetyl chloride, ketone or acetic anhydride in the presence of a Friedel-Crafts catalyst in an inert solvent at a temperature of $-10°$ C. to $30°$ C.

34. The process of claim 32, wherein the Friedel-Crafts catalyst is aluminum chloride or ferric chloride.

35. The compound according to claim 6, wherein A is methyl.

36. A perfume composition which contains a compound of the formula:

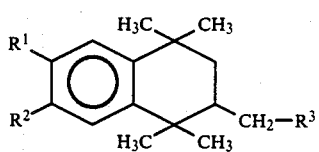
wherein either one of R¹ and R² is $C_1$-$C_4$ alkoxy and the other is acetyl and R³ is hydrogen or methyl in an optically active or racemic form and an acceptable exipient.
37. A compound of the formula:
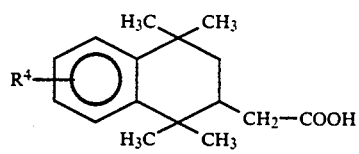
wherein R⁴ is hydrogen, $C_1$-$C_4$ alkyl or $C_1$-$C_4$ alkoxy present at either one of the 6- and 7- positions.
* * * * *